United States Patent [19]

Kaneko et al.

[11] Patent Number: 4,672,132

[45] Date of Patent: Jun. 9, 1987

[54] PROCESS FOR PRODUCING AN ALDEHYDELACTONE

[75] Inventors: Chikara Kaneko; Masayuki Sato, both of Sendaishi, Japan

[73] Assignee: Chisso Corporation, Osaka, Japan

[21] Appl. No.: 834,362

[22] Filed: Feb. 28, 1986

[30] Foreign Application Priority Data

Mar. 13, 1985 [JP] Japan ................................ 60-50141

[51] Int. Cl.$^4$ ........................................... C07D 307/93
[52] U.S. Cl. ................................. 549/311; 204/157.69
[58] Field of Search ..................... 204/158 R; 549/311

[56] References Cited

PUBLICATIONS

Paquette et al., CA 96 (3), 19700g.

*Primary Examiner*—Jane T. Fan
*Attorney, Agent, or Firm*—Wenderoth, Lind & Ponack

[57] ABSTRACT

A process for producing 3-oxo-6-formyl-2-oxabicyclo[3.3.0]-6-octene useful as an intermediate for producing prostaglandins, via a few steps from raw materials which can be relatively easily prepared. The process comprises subjecting 2,2-dimethyl-1,3-dioxin-4-one and cis-2-cyclopenten-1,4-diol to addition reaction in a solvent, preferably under a photo-irradiation, removing the solvent from the reaction mixture, adding water to the resulting adducts and reacting the resulting mixture on heating.

2 Claims, No Drawings

PROCESS FOR PRODUCING AN ALDEHYDELACTONE

BACKGROUND OF THE INVENTION

This invention relates to a process for producing 3-oxo-6-formyl-2-oxabicyclo[3.3.0]-6-octene.

3-Oxo-6-formyl-2-oxabicyclo[3.3.0]-6-octene (hereinafter referred to often as aldehydelactone) is a compound useful as an intermediate for producing prostaglandins which are physiologically active substances having a number of pharmacological activities such as blood pressure depression, anti-ulceration, bronchodilation, inhibition of gastric acid secretion, partus induction, etc.

The known processes for producing this aldehydelactone comprise a large number of reaction steps. For example, L. A. Paquette et al reported a process for producing the aldehydelactone consisting of 12 to 14 reaction steps (see Tetrahedron, Vol. 37, page 281 (1981)). The process, however, is not an easy one for producing the intermediate since it comprises a number of complicated reaction steps, and especially among these steps is included an ozonolysis reaction at a low temperature of −78° C.

The present inventors have conducted extensive research on a photo-addition reaction between a cis-2-cyclopenten-1,4-diol derivative and 2,2-dimethyl-1,3-dioxin-4-one, and have found that it is possible to obtain the aldehydelactone in a few steps without isolating the resulting photo-addition reaction products of cis-2-cyclopenten-1,4-diol, and thus have attained the present invention.

SUMMARY OF THE INVENTION

The object of the present invention is to provide a process for producing 3-oxo-6-formyl-2-oxabicyclo[3.3.0]-6-octene from raw materials which can be relatively easily prepared, via short steps consisting of easy unit reactions.

The present invention is directed to (1) A process for producing 3-oxo-6-formyl-2-oxabicyclo-[3.3.0]-6-octene which comprises subjecting 2,2-dimethyl-1,3-dioxin-4-one and cis-2-cyclopenten-1,4-diol to addition reaction in a solvent, removing this solvent from the reaction mixture, adding water to the resulting adducts and reacting the resulting mixture on heating.

(2) A process according to the above item (1) wherein said addition reaction is carried out under a photo-irradiation.

(3) A process according to the above item (1) wherein the addition reaction products of cis-2-cyclopenten-1,4-diol and 2,2-dimethyl-1,3-dioxin-4-one are used in the succeeding reaction without isolating them.

DESCRIPTION OF PREFERRED EMBODIMENTS

The production process of the present invention may be illustrated by the following reaction scheme:

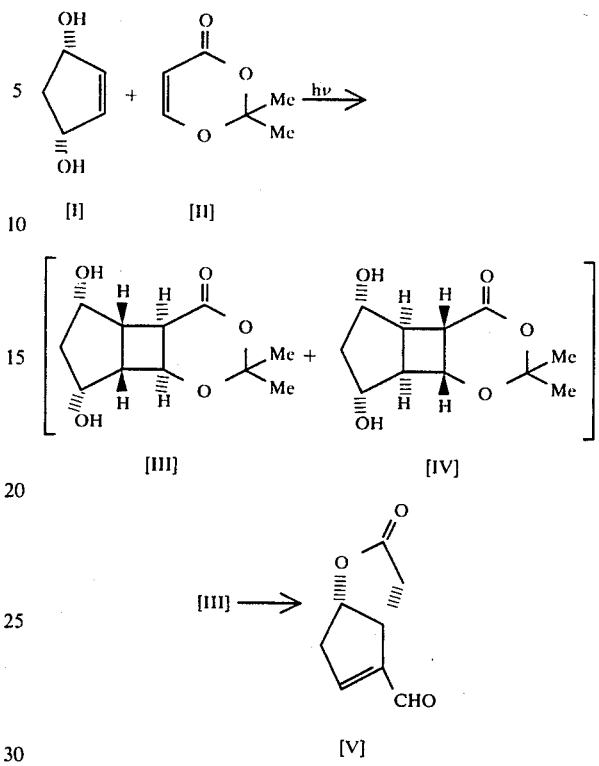

First, cis-2-cyclopenten-1,4-diol [I] (hereinafter referred to often as "diol") and 2,2-dimethyl-1,3-dioxin-4-one [II] (hereinafter referred to often as "dioxinone") are subjected to addition reaction in a suitable solvent, followed by adding water to the resulting adduct mixture and then heating the mixture under reflux, whereby it is possible to obtain 3-oxo-6-formyl-2-oxabicyclo[3.3.0]-6-octene [V] via reaction steps of deacetonization, ring opening, lactonization, dehydration, etc.

The addition reaction is particularly preferred to be conducted under photo-irradiation. As to the proportion of the raw materials used for the addition reaction, the molar ratio of diol to dioxinone may be $2/1$ or more, and in order to react dioxinone more effectively, it is preferred that the molar ratio be in the range of $5/1$ to $10/1$, that is, diol be used in large excess.

The solvent used in the present invention has no particular limitation as far as it is inert to the reaction. As the solvent used for the photo-addition reaction, esters such as ethyl acetate, butyl acetate, etc., ethers such as tetrahydrofuran, dioxane, etc., nitriles such as acetonitrile, propionitrile, etc., alcohols such as methanol, ethanol, etc. may be used. The quantity of the solvent used is in the range of 1 to 100 l, preferably 10 to 50 l, per mol of dioxinone as raw material.

The photo-addition reaction is carried out preferably at a temperature of 25° C. or lower in order to inhibit side reactions, and more preferably in the range of 0° to 20° C., although the reaction may be carried out even below 0° C., depending on the kind of the solvent, the irradiation conditions, etc.

As the light source for the irradiation, a high pressure or low pressure mercury vapor lamp may be preferably used. As the irradiation light, the light at the ultraviolet portion within a wavelength range of 254 to 300 nm is preferred. When a mercury vapor lamp is used as the light source, dioxinone as raw material is consumed in nearly the total quantity in an irradiation time of 0.1 to 3 hours, preferably 0.2 to one hour.

As for the material of the reaction vessel for the photo-addition reaction, it is preferred to avoid use of a material having a high absorbency at the above-mentioned ultraviolet portion, in order to utilize the irradiation light effectively.

The above photo-addition reaction products comprise two kinds of isomers expressed by the above formulas [III] and [IV], and these isomers are formed in a nearly equal proportion; this could have been presumed from the yields of the respective diacetate substances thereof. Namely, a technique of isolating these isomers has not yet been established, but the formation of the two isomers has been confirmed by converting the mixed adducts into their diacetates with acetic anhydride in the presence of pyridine, followed by chromatographical separation.

In the present invention, the adduct mixture is freed from a solvent contained therein by distilling off under reduced pressure or the like means, followed by adding water to the adduct mixture and then reacting the resulting mixture on heating, whereby the aldehydelactone is obtained from the isomer expressed by the formula [III] via reaction steps of hydrolysis, deacetonization, ring opening, lactonization, dehydration, etc. When water in a quantity of 2 to 400 mols, preferably 50 to 250 mols per mol of dioxinone as raw material is added to the adduct mixture, it is possible to complete the reaction of the latter step.

Since the formylcarboxylic acid originated from the isomer of the formula [IV] is not lactonized, it is so highly soluble in water that it remains together with diol as an unreacted raw material in the aqueous layer when the desired aldehydelactone is extracted; hence there is an advantage that the objective product can be very easily separated.

For extracting the objective aldehydelactone, halogenated hydrocarbons such as dichloromethane, ethylene chloride, chloroform, etc. may be preferably used.

As described above, the production process of the present invention comprises two unit steps including the addition reaction step and the lactonization step as the latter, but since the latter reaction step can be carried out without separating the resulting adducts from each other, followed by purification, the production process of the present invention can be regarded as a substantially one step production process.

Cis-2-cyclopenten-1,4-diol as one of the raw materials of the present invention may be prepared for example by way of shorter steps including photo-oxidation reaction of cyclopentadiene ( Japanese patent application laid-open No. Sho 52-97940/1977). 2,2-Dimethyl-1,3-dioxin-4-one as the other raw material may be prepared from Meldrum's acid as a commercially available reagent via formyl Meldrum's acid (U.S. Ser. No. 749,426; Japanese patent application laid open No. Sho 61-17580/1986).

According to the present invention, the aldehydelactone can be produced with a yield of about 40% based on the raw material dioxinone. The objective 3-oxo-6-formyl-2-oxabicyclo[3.3.0]-6-octene previously could have never been obtained without passing through a large number of steps, as described above, but according to the present invention a process for producing the compound using Meldrum's acid as a starting raw material, with a high overall yield of 15% or more has been established.

The present invention will be described in more detail by way of Example, but it should not be construed to be limited thereto.

EXAMPLE

A solution of cis-2-cyclopenten-1,4-diol (2.50 g, 25 mmols) and 2,2-dimethyl-1,3-dioxin-4-one (0.64 g, 5 mmols) dissolved in ethyl acetate (180 ml) was irradiated with a 400 W high pressure mercury vapor lamp using a Vycor glass filter for 30 minutes to carry out a photo-addition reaction, followed by distilling off the solvent from the reaction mixture under reduced pressure to obtain an oily substance as residue (3.474 g). To this oily substance (1.388 g) was added distilled water (20 ml), followed by heating the mixture under reflux for 2 hours, thereafter cooling, three times carrying out extraction operations with dichloromethane (10 ml), combining the extracts, drying over anhydrous magnesium sulfate, and concentrating under reduced pressure to obtain an oily substance (275 mg), which was then subjected to silica gel column chromatography and eluted with diethyl ether to obtain a colorless syrupy product (123 mg; yield 40%). This product had IR absorption spectra, $^1$H-NMR, MS and high resolution MS shown below:

IR (CHCl$_3$) (cm$^{-1}$): 1780(O—C=O), 1680(CH=O), 1620(C=C).

$^1$H-NMR(CDCl$_3$)δ(ppm): 2.82(2H, m, CH$_2$CO), 3.00(2H, m, CH$_2$—C=C), 3.72(1H, m, CH—C=C), 5.21(1H, m, CHOC), 6.88(1H, q, J=2Hz), 9.82(1H, s, CHO).

MS m/z: 152(M+), 124, 95, 79, 67 High resolution MS m/z: 152.0485 (Calculated from C$_8$H$_8$O$_3$: 152.0473).

The results of IR, $^1$H-NMR and MS accorded well with the data reported by Tsung-Tee Li et al (see J. Org. Chem., Vol. 46, page 111 (1981)); thus the substance obtained above could be identified as 3-oxo-6-formyl-2-oxabicyclo-[3.3.0]-6-octene.

What we claim is:

1. A process for producing 3-oxo-6-formyl-2-oxabicyclo-[3,3.0]-6-octene which comprises subjecting 2,2-dimethyl-1,3-dioxin-4-one and cis-2-cyclopenten-1,4-diol to a photo-addition reaction in a solvent, removing the solvent from the reaction mixture, adding water to the resulting adducts and heating the resulting mixture to produce the 3-oxo-6-formyl-2-oxabicyclo-[3.3.0]-6-octene.

2. A process according to claim 1, wherein the addition reaction products are used in the succeeding reaction without isolating them from the reaction mixture.

* * * * *